US00PP16540P2

(12) United States Plant Patent
Michalik

(10) Patent No.: US PP16,540 P2
(45) Date of Patent: May 16, 2006

(54) **VARIETY OF *PELARGONIUM* PLANT NAMED 'PACDO'**

(50) Latin Name: *Pelargonium zonale*
Varietal Denomination: Pacdo

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 85 days.

(21) Appl. No.: 11/043,799

(22) Filed: Jan. 26, 2005

(51) Int. Cl.
*A01H 5/00* (2006.01)

(52) U.S. Cl. ..... Plt./332

(58) Field of Classification Search ..... Plt./328, Plt./325
See application file for complete search history.

*Primary Examiner*—Kent Bell
(74) *Attorney, Agent, or Firm*—The Webb Law Firm

(57) ABSTRACT

A new and distinct flowering *Pelargonium* plant with dark leaves and striking pink flowers.

1 Drawing Sheet

Botanical classification: *Pelargonium zonale.*
Varietal denomination: 'Pacdo'.

BACKGROUND OF THE INVENTION

The present invention comprises a new and distinct cultivar of *Pelargonium zonale* known by the varietal name 'Pacdo'. The new variety was discovered in a selected breeding program in Dresden, Germany. The new variety is the result of a cross between two unnamed and unpatented selections from a collection of proprietary breeding plants. The purpose of the breeding program was to find a new variety with interesting color and good growth. The new variety differs from its parents primarily in flower color. The dark leaf color, flower form and purple eye are similar to 'Candy Lavender' (U.S. Plant patent application Ser. No. 09/739,023). The new variety differs from 'Candy Lavender' in flower color, plant height and branching characteristics. The new variety was first asexually reproduced in 2002 by cuttings and in vitro culture in Dresden, Germany. The new variety has been trial and field tested in Dresden and has been found to retain its distinctive characteristics and remain true to type through successive propogations. Characteristics distinguishable from other varieties include:

Unique flower color with an eye

Dark leaf color

Reddish peduncles and pedicels

DESCRIPTION OF THE DRAWING

The accompanying photographic drawing illustrates the new variety, with the color being as nearly true as is possible with color illustrations of this type.

DESCRIPTION OF THE PLANT

Figure 1:
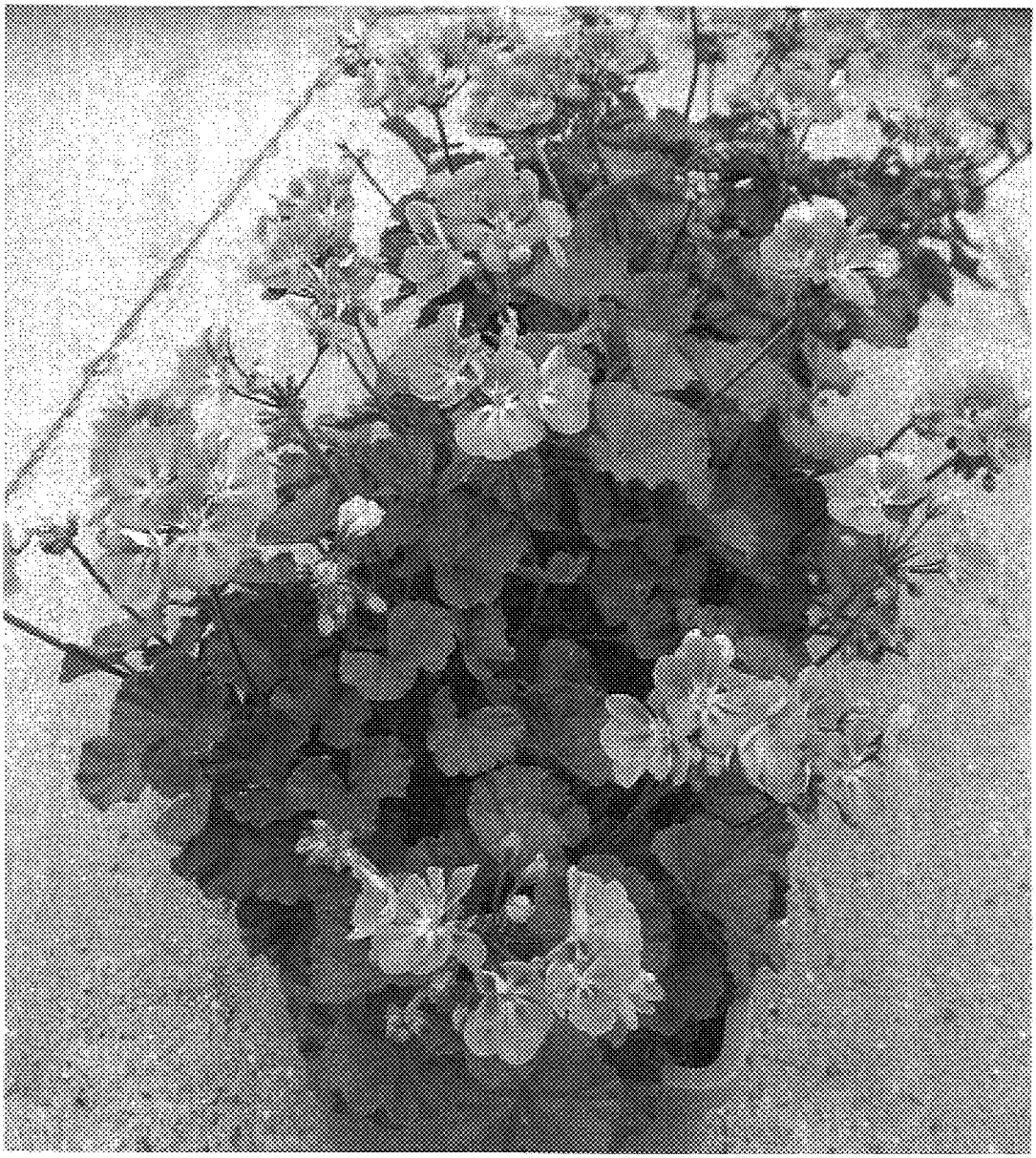

The following detailed description sets forth the characteristics of the new cultivar. The data that defines these characteristics were collected by asexual reproductions carried out in a warm greenhouse in Dresden, Germany. The color readings were taken on a plant indoors under natural light. The new variety was four months old where described.

Color references are primarily to the R.H.S. Colour Chart of The Royal Horticultural Society of London.

PLANT

Form: Erect.
Height: 15–17 cm from soil to top of foliage; 24–36 cm from soil to top of umbels.
Diameter: Approximately 20 cm.
Growth: Erect, well-branched with medium vigor.
Strength: Does not require artificial support; self-standing.
Time to initiate roots: About 8 days at 23° C.
Time to develop roots: About 25 days at 23° C.
Time to produce a finished flowering plant from a rooted cutting: About 10 weeks in a 10.5–12.0 cm container.

FOLIAGE

Arrangement: Alternate and opposite.
Leaves:
- *Size.*—Length: Approximately 3.5 cm. Width: Approximately 6.0 cm.
- *Shape.*—Overall: Typical zonal *pelargonium* leaf. Base: Wide open. Apex: Round.
- *Margin.*—Wavy, crenate.
- *Zonation.*—None present.
- *Texture.*—Hairy, with medium pubescence on both surfaces.
- *Aspect.*—Alternate and opposite.
- *Color.*—Young Leaves: Upper surface: 137A. Lower surface: 137B. Mature Leaves: Upper surface: 147A. Lower surface: Nearly 147A.
- *Ribs and veins.*—Venation: Net-like. Color: 143B.

Stipules:
- *Size.*—Medium.
- *Color.*—Green, 137A (both surfaces).

Petioles:
- *Color.*—Green, 146A.
- *Length.*—2.0–3.0 cm.
- *Diameter.*—Approximately 2.0 mm.

Main stem:
- *Length.*—15–18 cm.
- *Diameter.*—Approximately 9.0 mm.

*Color.*—Red-touched green, 146B with a hint of 166B.
*Internode length.*—1.0–1.5 cm.
*Texture.*—Hard.
*Pubescence.*—Medium.

Lateral branches:
*Internode length.*—1.0–2.0 cm.
*Texture.*—Hairy.
*Pubescence.*—Medium.
*Color.*—Green, 146B.

THE BUD

Number of buds per cluster: 25–30.
Shape:
*Cluster.*—Umbel.
*Individual bud.*—Elliptic.
Size:
*Cluster.*—Approximately 4.0 cm in diameter.
*Individual bud.*—Length: Approximately 1.3 cm. Width: Approximately 6.0 mm.

INFLORESCENCE

Natural flowering season: Spring and Summer until frost.
Blooming habit: Continuous.
Lastingness of an individual flower: 10 days maximum.
Size:
*Diameter.*—Approximately 10.0 cm.
*Depth.*—Approximately 8.0 cm.
Borne: Umbel; flowers on pedicel; pedicel on peduncle.
Number of flowers per umbel: 25–30.
Flowers:
*Position.*—Above foliage.
*Form.*—Flat and cupped.
*Size.*—Diameter: Approximately 4.5 cm. Depth: Approximately 1.2 cm.
*Petals.*—Number per flower: 8. Color: Upper surface: 57C. Lower surface: 57D. Tonality from a distance: Pink with an eye. Shape: Overall: Teardrop. Apex: Round. Base: Open. Size: Length: Approximately 2.8 cm. Width: Approximately 1.8 cm. Margin: Entire; rounded. Texture: Satin-like.

Petaloids:
*Number.*—Approximately 3.
*Shape, color, length and width.*—Like petals.

Pedicel:
*Length.*—Approximately 3.0 cm.
*Diameter.*—Approximately 2.0 cm.
*Color.*—178A.

Peduncle:
*Length.*—7.0–10.0 cm.
*Diameter.*—4.0 mm.
*Color.*—166A.
*Texture.*—Hairy.

Disease/pest resistance: No susceptibility to diseases or pests has been noted to date.
Temperature tolerance: Between 10° C.–30° C.
Fragrance: None.
Drought tolerance: None.

REPRODUCTIVE ORGANS

Stamens:
*Number per flower.*—6–8.
*Anthers.*—Shape: Elliptic. Length: 1.0 to 2.0 mm. Color: Pink.
*Filament.*—Length: Approximately 4.0 mm. Color: White.
*Pollen.*—Color: Orange. Amount: Uncountable.

Pistils:
*Numbers.*—One.
*Length.*—Approximately 1.0 cm.
*Stigma.*—Shape: Spider-like. Color: Pink. Size: Small to medium.
*Style.*—Length: Approximately 2.0 mm. Color: Light pink.
*Ovaries.*—Length: 1.0–2.0 mm. Width: 1.0–2.0 mm. Color: Green. Pubescence: Present.

I claim:

1. A new and distinct variety of *Pelargonium* plant substantially as shown and described.

* * * * *

UNITED STATES PATENT AND TRADEMARK OFFICE

CERTIFICATE OF CORRECTION

PATENT NO. : PP 16,540 P2
APPLICATION NO. : 11/043799
DATED : May 16, 2006
INVENTOR(S) : Michalik It is certified that error appears in the above-identified patent and that said Letters Patent is hereby corrected as shown below:

Column 4, Line 6: under Pedicel,
"Diameter: Approximately 2.0 cm."
should read
-- Diameter: Approximately 2.0 mm. --

Signed and Sealed this

Nineteenth Day of December, 2006

JON W. DUDAS
*Director of the United States Patent and Trademark Office*